United States Patent [19]

Narciso, Jr.

[11] Patent Number: 5,453,448
[45] Date of Patent: Sep. 26, 1995

[54] IN VIVO METHOD FOR ESTIMATING THE LIPID CONTANT OF AN ATHEROMATOUS LESION

[75] Inventor: Hugh L. Narciso, Jr., Santa Barbara, Calif.

[73] Assignee: PDT Cardiovascular, Inc., Santa Barbara, Calif.

[21] Appl. No.: 165,213

[22] Filed: Dec. 9, 1993

[51] Int. Cl.$^6$ .............................. A61K 47/00; A61N 1/30
[52] U.S. Cl. ................. 424/9.6; 604/19; 604/21; 606/2; 606/15; 514/824
[58] Field of Search ............................................. 514/824

OTHER PUBLICATIONS

91:116051 Medline 1990.
91:521953 Biosis 1991.
V. Fuster, et al., Clinical Pathoglogical . . . , Suppl. to Circulation 86, No. 6, 1992.
J. J. Badimon, Coronary Atherosclerosis . . . Suppl. to Circulation 87, No. 3,1993.
E. Falk, Why Do Plaques Rupture, Suppl. to Circulation 86, No. 6, 1992.
D. Kessel, et al., Porphyrin Accumulation . . . , Photochem. Photobiol. 40 No. 1 1984.

Primary Examiner—Paul J. Killos
Attorney, Agent, or Firm—Michael G. Petit

[57] ABSTRACT

Cardiovascular disease is the leading cause of death in the United States. Interpreting the relative danger of a lesion within the vasculature is limited by a lack of information on the composition of lesion. It is believed that a lesion which is high in lipids is more prone to rupture followed by thrombosis than a stable highly calcific, fibrotic, high grade stenosis. To address this recent hypothesis, a method of diagnosing and treating the most problematic vascular lesions is presented. The method employs the selective uptake of a lipophilic fluorescent compound by a lesion followed by the application of excitation light to the fluorescent compound-ladened lesion causing the fluorescent compound to emit fluorescence light. The intensity of the fluorescence light indicates the lipid content and/or the fibrous cap thickness, thus providing information on the potential danger of the lesion and enabling the clinician to treat the lesion in a manner which provides the patient with the best chance for clinical success.

10 Claims, No Drawings

IN VIVO METHOD FOR ESTIMATING THE LIPID CONTANT OF AN ATHEROMATOUS LESION

BACKGROUND OF THE INVENTION

1. Field of the Invention

This invention relates to a method of diagnosing and treating cardiovascular disease and, more particularly, to the use of lipophilic fluorescent compounds to identify areas of atherosclerotic plaque containing high levels of lipids and/or exhibiting high levels of metabolic activity.

2. Reference to Copending U.S. Pat. application

Reference is made herein to copending U.S. Pat. application Ser. No. 07/930,860 filed Aug. 14, 1992 entitled: "Method for Treating Cardiovascular Disease Through Adjunctive Photodynamic Therapy" by the present inventor.

3. Prior

According to the American Heart Association over six million Americans suffer from cardiovascular disease. More than 400,000 Percutaneous Transluminal Coronary Angioplasties were performed in 1992 and an additional 300,000 Coronary Artery Bypass Graft surgeries performed.

Coronary artery disease is thought to be initiated by a disruption of fatty streaks which form early in life on the wall of a blood vessel; which disruption, in turn, promotes thrombus formation. Over time the thrombus becomes organized and provides structure for the accumulation of fatty lipids, foam cells, cholesterol, calcium, fibrin, and collagen. A fibrous cap forms over this collection of lipid-rich material. Periodically this fibrous cap ruptures or ulcerates releasing some of underlying contents and exposing the plaque constituents to the flowing blood. Growth factors within the blood initiate the migration of smooth muscle cells (SMC's) from the media to the intima of the blood vessel where proliferation of the SMC's begins. The ulcerated plaque induces the deposition of platelets and thrombus formation in a "response to injury" mode. This cycle recurs until eventually the plaque ruptures, the distal coronary vessel is occluded by an intramural thrombus and a heart attack occurs. (For further details, see, for example, V. Fuster, et al, *Clinical-Pathological Correlations of Coronary Disease Progression and Regression, Supplement to Circulation*, Vol. 86, No. 6, 1992:III-1-11 and *JJ Badimon, Coronary Atherosclerosis, A Multifactorial Disease, Supplement to Circulation*, Vol. 87, No. 3, 1993:II-3-II-16).

Years of research have revealed the above-described scenario concerning the genesis and progression of atherosclerotic disease. More recent research suggests that the severity of a stenosis or a lesion within a vessel may not be the greatest predictor of the potential danger that the lesion will rupture and cause a heart attack. Some high grade stenoses are fibrotic and/or calcified and therefore relatively stable, while a less severe stenosis which is high in lipid content may be more prone to rupture causing vessel occlusion. (See, for example, *E. Falk, Why Do Plaques Rupture?, Supplement to Circulation*, Vol. 86, No. 6, 1992:III-30-III-42). This view represents a dramatic departure from the theory that the most high grade stenosis is the most dangerous lesion. For this reason, being able to prospectively detect the levels of lipids within a lesion is potentially of greater value to a clinician than a knowledge of the degree of stenosis.

Present methods of assessing the severity of coronary artery disease include angiography, angioscopy, intravascular ultrasound, color flow Doppler ultrasound and spectroscopy. Angiography, the presently preferred method of imaging a stenosis within a vessel, provides a flow map through the use of a radio-opaque dye. While angiography is useful for indicating areas of flow the method provides no information regarding the tissue underlying the surface of the inner lining of the vessel. Angiography provides a two dimensional projection of a three dimensional artery and therefore is orientation dependent and limited in usefulness.

Angioscopy provides a video-displayed image of the internal surface of the artery. Again, the information is limited to topography with no sub-intimal information provided. Since angioscopy requires a blood free environment for viewing, the blood must either be displaced or occluded with a balloon device or flushed away with a constant flow of a transparent fluid such as saline. Both situations lead to ischemic conditions in distal tissue.

Intra-Vascular Ultrasound, (IVUS), is a promising morality for assessing the severity of an atherosclerotic lesion. The information provided is sub-intimal allowing differentiation between the layers of the vessel due to the echogenic or sonic absorption characteristics of the layers of the underlying tissue. Highly echogenic materials such as calcium are easily identified below the surface of the vessel wall. Differentiation between soft tissues comprising the plaque are less defined. At present, the lipid content of a lesion cannot be assessed through the sonic properties of the tissues.

Extravascular ultrasound or color flow Doppler, as with angiography, provides a flow map. The flow map obtained with extravascular ultrasound provides less detail than angiography, but the flow map can be observed over a long period of time due to the noninvasive nature of the procedure.

Spectroscopy has been tested in the human coronades to differentiate plaque fluorescence from normal wall fluorescence. However, since the plaque invades the coronary wall to such an extent, there is little spectroscopic difference. Thus, it is difficult to identify where the plaque begins and the normal arterial tissue ends. Such "smart lasers" have for the most part disappeared from the clinical arena.

Fluorescence has been a useful tool in vitro for distinguishing between plaque and normal artery when enhanced with an exogenously administered chromophore or fluorophore. (See, for example, *D Kessel, et al, Porphyrin Accumulation by Atheromatous Plaques of the Aorta, Photochem. Photobiol.*, Vol. 40, No. 1, 1984:59–61). The use of exogenous dyes has been proposed by Prince, et.al., as a clinical guidance system for angioplasty (LG Prince, et al, *Laser-Induced Fluorescence Detection of Atherosclerotic Plaque with Hematoporphyrin Derivative Used as an exogenous Probe, J. of Vascular Surgery*, Vol. 7, No. 4, 1988:500–506).

Spears, in U.S. Pat. No. 4,773,899 has proposed using Hematoporphyrin Derivative (HpD) as an aid in identifying the location of plaques, ex vivo, within the arteries. HpD, a hydrophilic photosensitizer, demonstrates some selectivity to uptake by atherosclerotic plaques regardless of the biochemical make-up of the plaque. Since HpD only has the ability to locate a plaque without providing information on the biochemical make-up of such a lesion, the Spears method cannot be used to prospectively determine the lipid content and thus the potential danger of a particular lesion.

With the present understanding of atherosclerosis and the events leading to restenosis following interventional revascularization, the biochemical composition or metabolic activity of a cardiovascular lesion is very important to the diagnosis and selection of the best course of treatment. This is a dramatic departure from the previous theory which maintains that the most dangerous cardiovascular lesion is the lesion which is the most severely stenosed. As stated earlier, the present methods of assessing the severity of a lesion of the vasculature, such as angiography, are based on the old theory that a higher grade stenosis implies a more dangerous lesion. New methods of evaluating lesions are required to provide data concerning the lipid content of a lesion because recent research shows that greater lipid content indicates a potentially more dangerous lesion. In vitro methods of assessing the presence or absence of atherosclerotic or restenotic disease are not clinically useful but may provide some insight into defining a clinical method for assessing the composition and metabolic activity of a plaque; therefore, providing a method of identifying and prospectively guiding the clinician decision making process.

SUMMARY OF THE INVENTION

It is an object of the present invention to provide a clinical method of identifying an atherosclerotic lesion with the use of a fluorescing compound.

It is a further object of the present invention to provide a clinical method of prospectively determining the potential danger associated with an atherosclerotic lesion with the use of a lipophilic fluorescing compound.

It is a further object of the present invention to provide a clinical method for prospectively determining the lipid content of an atherosclerotic lesion.

It is a further object of the present invention to provide a clinical method for determining the metabolic activity of either an atherosclerotic plaque or a restenosing lesion by incorporation of a lipophilic fluorescent compound into hyperproliferating cells.

It is yet a further object of the present invention to provide a clinical method for treating an atherosclerotic or restenotic lesion based on the information provided by the diagnostic use of a lipophilic fluorescent compound which also has properties of a photosensitizer.

The present invention solves the above and other problems by providing a composition and method for diagnosing, assessing and treating atherosclerotic and restenotic disease of the vasculature by analyzing the lipid content of the atherosclerotic tissue. The method comprises the steps of (a) administering a lipophilic fluorescent compound, which may or may not have the properties of a photosensitizer (PS) to a patient; Co) allowing the fluorescent/PS compound to accumulate in the diseased tissues while clearing from the healthy tissues; then (c) delivering low level excitation light to the suspect lesion and (d) detecting the fluorescence signal emitted by the fluorescent compound following the absorption of excitation light by the fluorescent compound.

DESCRIPTION OF THE PREFERRED EMBODIMENT

Many fluorescing compounds such as Tin Ethyl Etiopurpurin are hydrophobic and thus lipophilic and exhibit an affinity for atherosclerotic tissue. A bias in the uptake of such lipophilic fluorescent compounds toward lipid-rich plaques can be exploited to indicate the presence and extent of lipid involvement in a particular lesion. The intensity of the fluorescence signal may also provide information on the thickness of the fibrous cap which segregates and partitions the lipid core of the plaque from the flowing blood, thus indicating the potential for the fibrous cap to rupture. In addition to the lipophilic properties of these fluorescing compounds, they exhibit an affinity for cells which hyperproliferate in response to angioplasty injury such as smooth muscle cells. This phenomenon has been described in detail in co-pending U.S. Pat. application No. 07/930,860, U.S. Pat. No. 5,298,018 by the present inventor. For the above reason, this method can be used for the diagnosis, assessment and treatment of both atherosclerosis (the primary disease) and restenosis (secondary disease induced by treatment of the primary disease).

The administration of a lipophilic fluorescent compound can be performed by any one of a variety of methods. Bolus injection along with oral and topical administration have all been used clinically to systemically deliver fluorescent compounds and fluorescent compounds/photosensitizers for the treatment of cancer and psoriasis. Researchers are presently investigating alternate local delivery schemes to deliver like compounds. Such local delivery methods include implantable and removable stents made from metals such as stainless steel, tantalum or Nitinol; bio-absorbable materials such as polycaprolactone, and biological materials such as collagen. Local delivery can also employ balloon catheters having porous balloons thereon, dual balloon catheters and iontophoretic devices. Or a surface-coated catheter or balloon may be employed to deliver such lipophilic fluorescent compounds topically to a lesion. Still others have proposed using microparticles impregnated with pharmaceuticals for local delivery (see, for example, U.S. Pat. No. 5,171,217, March, et al).

For the selectivity of the fluorescent compound/PS to be optimum, a latency period is required which permits the fluorescent compound to clear from healthy cells, serum or blood while being retained by atypical cells. Data acquired from studies involving the use of Photodynamic Therapy to treat cancer suggests that the time for clearance is optimum from 24–72 hours, but applicable from 3 hours to one week (U.S. Pat. No. 4,932,934, Dougherty, et al).

Excitation light of a proper wavelength for inducing fluorescence in such lipophilic fluorescent compounds can be generated by a number of sources such as lasers, arc lamps, and Light Emitting Diodes (LEDs). Suitable excitation wavelengths for stimulating fluorescence have been demonstrated from 350–800 nm, but are not limited to this range. The optimum excitation wavelength will vary depending on the light absorption spectra of the particular lipophilic fluorescent compound employed.

Various catheters can be used to deliver and receive light for this procedure. U.S. Pat. No. 5,169,395, to Narciso and U.S. Pat. No. 5,196,005 to Doiron, et al describe such catheters. These include light diffusing tip catheters, flat polished or cleaved fiber optic catheters, or side firing light catheters. Transparent balloons may be incorporated into a light diffusing catheter to surround the light diffuser element. The balloon is then inflated resulting in the displacement of tissue (or light absorbing blood) from around the light diffuser tip enabling irradiation of a lesion on the vessel wall.

The fluorescent signal emitted by suitable lipophilic fluorescent compounds such as tin ethyletiopurpurin in response to optical excitation has been demonstrated from 400–800 nm, but is not limited to this range. The same optical catheter used to deliver the excitation light to the lesion under study can be used to receive the fluorescence signal from the lesion. (See for example U.S. Pat. No. 5,217,456, to Narciso).

Fluorescent compounds/photosensitizers have demonstrated an affinity for hyperproliferating cells such as smooth muscle cells post angioplasty. The use of such fluorescent/PS compounds have been proposed in conjunction with light activation for the prevention of restenosis (Co-pending U.S. Pat. application No. 07/930,860, to Narciso). The same affinity for hyperproliferating cells can be exploited for the diagnostic determination of the lipid content of a lesion.

Once the cardiovascular disease has been identified, and the risk assessed by evaluating the lipid content of the lesion, an appropriate therapeutic regimen may be selected. This can include Photodynamic Therapy of the fluorescent/PS compound-ladened plaque, photothermal therapy, photo-inhibition of proliferating/migrating smooth muscle cells, photomutegenic therapy, photochemical therapy, balloon angioplasty, laser angioplasty, heated balloon (RF, ultrasound or laser) angioplasty, mechanical atherectomy, laser atherectomy, the insertion and deployment of stents in all varieties, or pharmacologic means. Pharmacologic treatments include anti-coagulants, fibrinolytic, thrombolytic, anti-inflammatory, anti-proliferative, immunosuppressant, collagen inhibitor, or endothelium cell growth promoter. Or, if the lipid content of a lesion is low, and/or the fibrous cap thick, it may be advisable to do nothing.

The above is a detailed description of a particular embodiment of the invention. It is recognized that departures from the disclosed embodiment may be within the scope of the invention and that obvious modifications will occur to a person skilled in the art. The full scope Of the invention is set out in the claims that follow and their equivalents. Accordingly, the claims and specification should not be construed to unduly narrow the full scope of protection to which the invention is entitled.

What I claim is:

1. A in vivo method for estimating the lipid content of an atheromatous lesion on the wall of a blood vessel comprising the steps of:
   (a) introducing a fluorescent lipophilic compound into the body of a patient;
   (b) waiting for a latency period to allow said lipophilic fluorescent compound to accumulate in the atheromatous lesion while being substantially cleared from other tissue;
   (c) delivering excitation light to the atheromatous lesion to cause said fluorescent compound to emit fluorescent light;
   (d) remotely sensing the fluorescent light.

2. The method of claim 1 where the fluorescing compound also exhibits the properties of a photosensitizer.

3. The method of claim 1 wherein the administration of fluorescing compound is systemic.

4. The method of claim 1 where the administration of the fluorescing compound is local.

5. The method of claim 1 where the latency period is 3–168 hours with 24–72 hour being preferred.

6. The method of claim 1 where said excitation light is produced by a source selected from the group consisting of a laser, arc lamp, Light Emitting Diode system or chemoluminescence agent.

7. The method of claim 1 wherein the fluorescence light has a wavelength between 400–1100 nm.

8. The method of claim 1 wherein the fluorescence light is detected by a catheter having detecting means thereon selected from the group consisting of a light diffusing tip, a balloon light diffusing tip catheter, a polished or cleaved optical fiber, or an optical fiber modified to emit light at an angle 30–90 degrees from the optical fiber axis.

9. The method of claim 1 wherein said excitation light is delivered to the atheromatous lesion by an intravascular catheter.

10. The method of claim 1 wherein the fluorescing compound is both lipophilic and has an affinity for hyperproliferating smooth muscle cells.

* * * * *